United States Patent [19]
Hart et al.

[11] Patent Number: 4,772,551
[45] Date of Patent: Sep. 20, 1988

[54] METHOD AND TEST KIT FOR DETECTING A TRICHOTHECENE USING NOVEL MONOCLONAL ANTIBODIES

[75] Inventors: L. Patrick Hart, Lansing; James J. Pestka, East Lansing; Elie H. Gendloff, Lansing, all of Mich.

[73] Assignee: Neogen Corporation, Lansing, Mich.

[21] Appl. No.: 813,499

[22] Filed: Dec. 26, 1985

[51] Int. Cl.$^4$ .......................... G01N 33/53

[52] U.S. Cl. .......................... 435/7; 435/28; 435/810; 436/518; 436/548; 436/808; 436/822; 935/93; 935/104; 935/110; 530/388; 530/807; 530/809

[58] Field of Search .......................... 424/85, 88; 435/7, 28, 435/810, 929; 436/518, 531, 548, 808, 822; 935/93, 104, 110; 530/388, 807, 809

[56] References Cited

U.S. PATENT DOCUMENTS

| | | | |
|---|---|---|---|
| 4,376,110 | 3/1983 | David | 436/529 |
| 4,443,549 | 4/1984 | Sadowski | 935/93 |
| 4,689,400 | 8/1987 | Finkelman | 530/389 |

FOREIGN PATENT DOCUMENTS

| | | | |
|---|---|---|---|
| 8602736 | 5/1986 | PCT Int'l Appl. | 435/7 |
| 2075987 | 11/1981 | United Kingdom | 935/93 |

OTHER PUBLICATIONS

Hunter, Chemical Abstracts 102:76957n.

Feuerstein J. Clinical Investigations 76(6), pp. 2134–2138 (1985).

Hunter, Applied & Environmental Microbiology 49(1), pp. 168–172, 1985.

Chu, F. S. et al., Applied & Evironmental Microbiol. 37:104–108 (1979).

Lee, S. et al., J. Assoc. Off. Anal. Chem. 64:156–161, 684–688 (1981).

Gendloff, E. H. et al., Appl Environ Microbiol 47:1161–1163 (1984).

Pestka, J. J. et al., Appl Environ Microbiol 40:1027–1031 (1980).

Oi, V. T. et al., Selected Methods in Cellular Immunology, W. H. Freeman, U.S.A., pp. 351–372 (1980).

Kennett, R. H., Monoclonal Antibodies, pp. 365–367 (1980).

Sugasaware, R. J. et al., J. Immunol Methods 79:263–275 (1985).

Fan, T. S. et al., J. Food Protection 47:964–967 (1984).

Fontelo, P. A. et al., Appl Environ Microbiol 45: 640–642 (1983).

Pestka, J. J. et al., Am Oil Chem Soc 58:940A–944A (1981).

*Primary Examiner*—Robert J. Warden
*Assistant Examiner*—Robert Benson
*Attorney, Agent, or Firm*—Ian C. McLeod

[57] ABSTRACT

A method for producing monoclonal antibodies to a trichothecene mycotoxin which are used in a test kit and method of testing are described. The method for producing the monoclonal antibodies uses repeated administration, preferably subcutaneously of a trichothecene polypeptide to a murine and production of a hybridoma to generate the monoclonal antibodies. Trichothecenes are detected in foods and the like using the test kit and method.

10 Claims, No Drawings

METHOD AND TEST KIT FOR DETECTING A TRICHOTHECENE USING NOVEL MONOCLONAL ANTIBODIES

BACKGROUND OF THE INVENTION (1) Field of the Invention

The present invention relates to a method for producing novel monoclonal antibodies against a trichothecene and to a test kit and method which use these monoclonal antibodies to detect the presence of a trichothecene in foods and the like. In particular the present invention relates to monoclonal antibodies produced by repeated introduction, preferably subcutaneously, of a trichothecene polypeptide into a murine over a period of time so that polyclonal antibodies are developed in the blood serum of the murine and then by the production of hybridomas from spleen cells of the murine which generate the monoclonal antibodies.

(2) Prior Art

Mycotoxins are chemical substances produced by fungi which affect the health of humans and animals. The fungi are not involved in the disease process and are often absent from the food source at the time of poisoning. Mycotoxins are usually quite stable and remain active after processing and cooking. Mycotoxins or their metabolic products appear as residues in meat, milk and eggs making them unfit to eat.

The aflatoxins are probably the best known mycotoxins because of their mutagenic and carcinogenic properties. The fluorescent properties of the aflatoxins make detection fairly easy. Recently, a group of mycotoxins known as the trichothecenes have become the focus of attention because of their detection in corn and small grains, and because the trichothecenes may have been used for chemical warfare. The trichothecenes are difficult to identify because they do not contain a functional group which permits easy identification by spectrophotometric methods, and they do not react specifically with any reagent which provides a colorimetric assay. Thin layer chromatography is frequently used to detect trichothecenes, but this method is relatively insensitive and semi-quantitative due to difficulty in uniformly spraying the plates. Gas liquid chromatography (GLC), fluorodensitometry and GLC-mass spectroscopy (GL-MS) have been used successfully but do not lend themselves to application in the field. Only GL-MS will positively identify a suspected trichothecene. These procedures are also time consuming and expensive.

Trichothecenes are produced by several species of fungi, but most predominantly by Fusarium sp. There are at least 37 known natural trichothecene derivatives, six of which are somehow involved in Fusarium toxicosis.

The trichothecenes, when applied to the shaved skin of a rat or a rabbit, produce a strong dermititic reaction. This crude bioassay is sensitive but not specific. The reaction is characterized by severe local irritation, inflammation, desquamation, subepidermal hemorrhaging, and general necrosis. When given orally or by intraperitoneal injection the trichothecenes are acutely toxic at low concentrations. For example, T-2 toxin in rats has an $LD_{50}$ of 3.0 mg/Kg body weight when administered by intraperitoneal injection, and 3.8 mg/Kg when administered orally.

General symptoms of test animals orally dosed with trichothecenes are listlessness, development of diarrhea, and rectal hemorrhaging. Necrotic lesions can develop in the mouth parts. The mucosal epithelium of the stomach and small intestines erode, accompanied by a hemorrhage which can develop into a severe case of gastrointestinitis, followed by death. The cells of the bone marrow, lymph nodes, and intestines undergo a pathological degeneration. In large animals, massive hemorrhages develop in the lumen of the small intestines. The trichothecenes are also more potent protein inhibitors than the antibiotics puromycin and cycloheximide. The effects of ingesting sub-lethal doses of the trichothecenes over a long period of time are not known. One of the trichothecenes, T-2, is believed responsible for alimentary toxic aleukia (ATA) which caused thousands of deaths in Russia (1944–47) when Fusarium infected grain was ingested.

Several immunological studies have been done on mycotoxins (Chu, F. S., S. Grossman, Ru-Dong Wei, and C. Mirocha. Applied and Environmental Microbiology 37:104–108 (1979); Lee, S. and F. S. Chu. J. Assoc. Off. Anal. Chem. 64:156–161 (1981); and Lee, S. and F. S. Chu. J. Assoc. Off Anal Chem 64:684–688 (1981)). Highly specific polyclonal antibodies were produced in rabbits to a bovine serum albumin (BSA) conjugate to Ochratoxin A, BSA conjugates to Aflatoxins $B_1$, $B_2$, and $M_1$ derivatives, and a BSA conjugate to a T-2 derivative. Specific polyclonal antibodies were also produced in rats and goats immunized with an aflatoxin $B_1$-BSA conjugate but titer levels were lower than in the analogous antisera from rabbits. A highly sensitive radioimmunoassay (RIA) was developed for these systems. Using polyclonal antibodies produced to aflatoxin $B_1$ and ochratoxin A, a sensitivity of 5–10 ppb was obtained with crude corn, wheat, urine and blood extracts.

It was therefore decided that it would be advantageous to use monoclonal antibodies for conducting the tests. This would provide an advantage over more traditional serological techniques due to the possibility that hybridomas could produce unlimited amounts of highly uniform monoclonal antibodies with specificities comparable with the best rabbit antiserum. These monoclonal antibodies could then be used in the development of a colorimetric commercial assay system for the mycotoxins, such as Enzyme Linked Immunoabsorbant Assay (ELISA) or fluorescent antibody tests.

OBJECTS

It is therefore an object of the present invention to provide a highly specific assay method and test kit for a trichothecene using a monoclonal antibody. Further it is an object of the present invention to provide novel monoclonal antibodies against a trichothecene and a method for producing them. These and other objects will become increasingly apparent by reference to the following description.

GENERAL DESCRIPTION

The present invention relates to an improvement in a test kit for detecting a trichothecene antigen using an immunoassay wherein a label on an antigen or an antibody is detected to determine the unknown antigen, which comprises: providing in the test kit a monoclonal antibody to the trichothecene wherein the antibody is derived by repeatedly introducing a trichothecene polypeptide conjugate into a murine so that polyclonal antibodies are developed in the blood serum of the murine, by forming a hybridoma with spleen cells from the murine and myeloma cells and by isolating the hybridoma which produces a monoclonal antibody which specifically binds the trichothecene.

Further the present invention relates to an improvement in a method for testing for an unknown trichothecene in an immunoassay wherein a labeled known antigen or an antibody is used to determine an unknown antigen which comprises: providing a monoclonal antibody to the trichothecene wherein the monoclonal antibody is derived by repeatedly introducing a trichothecene polypeptide conjugate into a murine so that polyclonal antibodies are developed in the blood serum of the murine, by forming a hybridoma with spleen cells from the murine and myeloma cells and by isolating the hybridoma which produces the monoclonal antibody which is specific for the trichothecene; and testing for the unknown trichothecene using the monoclonal antibody.

The present invention also relates to an improvement in a method for producing monoclonal antibodies to a trichothecene compound by harvesting spleen cells of a murine which has been immunized with an antigen and fusing the spleen cells to myeloma cells to form a hybridoma cell which produces the antibody which comprises: repeatedly introducing into the murine a dosage of a trichothecene and polypeptide conjugate as the antigen so that polyclonal antibodies are developed in the blood serum of the murine; harvesting the spleen cells of the murine; forming the hybridoma with the spleen cells of the murine fused to the myeloma cells; and selecting the hybridoma cell which produce the monoclonal antibody against the trichothecene compound.

Finally the present invention relates to specific monoclonal antibodies against a trichothecene, particularly T2 toxin, produced by hybridomas prepared by the preceding method. In particular the present invention relates to hybridoma IVI-10092 and to hybridomas produced with the preferred murine myeloma ATCC TIB 18. The ATCC is the American Type Culture Collection in Rockville, Md. and the IVI is In Vitro International, Inc., 7885 Jackson Road, Ann Arbor, Mich. 48103. The monoclonal antibodies are kappa light chain, IgG, class antibodies.

The term "polypeptide" as used herein includes natural proteins as well as synthetically produced compounds which have varying molecular weights. Bovine serum albumin and ovalbumin are examples of proteins and poly L lysine is an example of a synthetically produced compound. The purpose of these proteins is to concentrate the trichothecene on the surface of the polypeptide so that polyclonal antibodies are developed in the blood serum of the mice.

To produce the monoclonal antibodies, the mice are treated with the polypeptide trichothecene conjugate so as to develop polyclonal antibodies in the blood serum of the murine. Preferably the mice are injected subcutaneously at about two to four (2 to 4) week intervals with between 0.1 to 5 mg (most preferably 0.5 to 1 mg) of a trichothecene bovine albumin conjugate. Spleen cells from the mice are isolated and fused to the myeloma cells to produce a hybridoma. The cells are then screened for specific monoclonal antibody production against a trichothecene.

Surprisingly it has been found that the treatment of the mice is preferably by subcutaneous injection, rather than by intravenous or intraperitoneal injection, in order to obtain the most effective results. Repeated administration over a period of time is necessary. Other methods of administration can be used; however, care must be taken since the trichothecenes are poisonous to the mice. The chances for success in producing a useful hybridoma using the other methods are poorer than when subcutaneous injection is used.

SPECIFIC DESCRIPTION

The following is a description of the preferred embodiment of the present invention.

MATERIALS AND METHODS

Materials. All inorganic chemicals and organic solvents were reagent grade or better. Bovine serum albumin (BSA) (fatty acid free and fraction V), polyoxyethylenesorbitan monolaurate (Tween 20), 2,2'-azinodi(3-ethylbenzthiazoline sulfonic acid) (ABTS), ovalbumin (crude and fraction VII), dicyclohexylcarbodiimide, N-hydroxysuccinimide, poly-1-lysine (MW 22000) (PLL), aminopterin, 8-azaguanine, polyethylene glycol MW 1450 sodium pyruvate, insulin, B-mercaptoethanol, oxalocacetate, pristane, thymidine, and hypoxanthene were obtained from Sigma Chemical Co., St. Louis, Mo.; Freund's adjuvants from Difco, Detroit, Mich.; goat antimouse IgG conjugated to horseradish peroxidase (antimouse peroxidase) from Cooper Biomedical, Malvern, Pa.; immunoassay microtiter plates (immunoplates) from Nunc Intermed, Roskilde, Denmark; filter paper from Whatman, Inc., Clifton, N.J.; T-2 from MycoLab Co., Chesterfield, Mo., and various cell culture reagents from Gibco Laboratories, Grand Island, N.Y.

Preparation of Conjugates. T-2 was converted to T-2-hemisuccinate (T-2HS) and conjugated to fatty acid-free BSA by the method of Chu et al (Chu, F. S., S. Grossman, R.-D. Wei, and C. J. Mirocha. Appl. Environ. Microbiol. 37:104–108 (1979)). T-2HS was also conjugated to ovalbumin (fraction VII) and PLL via an activated ester intermediate. 1 mg of T-2 hemisuccinate (T-2 HS) was mixed with an equimolar amount of both dicyclohexylcarbodiimide and N-hydroxysuccinimide in 0.1 ml dry tetrahydrofuran, then stirred 30 to 60 minutes at room temperature. The precipitate was filtered using Whatman #1 filter paper, and then washed with 2 to 3 ml tetrahydrofuran. The tetrahydrofuran was evaporated and the residue dissolved in 0.2 ml dimethylformamide. Dropwise addition to 5 mg polypeptide (Poly-L-lysine, or Bovine Serum Albumin) dissolved in 0.5 ml of 0.13 M sodium bicarbonate followed. This mixture was slowly stirred 30 minutes then dialyzed for 3 days against frequent changes of 0.1 M sodium bicarbonate.

Immunization protocols. Two different immunization protocols were compared. Both involved the T-2HS-BSA conjugate described above and three BALB/c mice. In the first group, protocol A, 100 ug conjugate in 0.1 ml saline was emulsified with 0.1 ml Freund's complete adjuvant and injected into the peritoneal cavity of each mouse. Booster injections were made at one month intervals as above except the Freund's adjuvant was incomplete. In the second group, protocol B, 1 mg conjugate in 0.5 ml saline was injected subcutaneously into the shoulder. These were repeated at two week intervals, except 0.5 mg conjugate was used. Both groups were bled through the tail vein 79 days after the initial injection. The red cells were pelleted and the serum was diluted and tested for T-2 antibody activity as described below.

CEIA. A competitive indirect enzyme immunoassay (EIA) procedure was always used in screening for antibody activity against T-2. The assay method for screening included the steps of binding a trichothecene conjugate in a well; introducing an antibody into the well containing an unbound trichothecene so that the antibody competitively binds to the unbound trichothecene and to the trichothecene conjugate to form a trichothecene complex of the trichothecene conjugate and antibody in the well; reacting an enzyme-antibody complex with the trichothecene complex in the well; and reacting the enzyme of the enzyme antibody complex with a substrate to determine the amount of the unbound trichothecene. In the preliminary assay of the mouse serum, T-2 was mixed with the antibody in some instances in order to test for the specificity of the antibody for T-2. In these assays, the free T-2 was bound to the antibody before it could bind to the T-2 conjugate in the well.

In particular, T-2HS-PLL or T-2HS-ovalbumin conjugate (200 ul), diluted to 2.5 ug/ml in 50 mM carbonate-bicarbonate buffer, pH 9.6, was placed in each well of 96-well immunoplates. The PLL conjugate was used in initial hybridoma screening and the ovalbumin conjugate was used later. The plates were incubated overnight at 4° C. They were then washed with sodium phosphate buffered saline (PBS-0.1 M; pH 7.5) containing 0.05% Tween 20 as previously described (Gendloff, E. H., J. J. Pestka, S. P. Swanson, and L. P. Hart, Appl. Environ. Microbiol. 47:1161–1163 (1984)), except a 12 hole aspirator was used. After washing, 200 ul PBS containing 1% (wt/vol) ovalbumin (PBS-ovalbumin) was added to each well after insoluble matter in the preparation was removed by a low speed centrifugation. After incubation for 30 minutes at 37° C., the plates were washed as above. Next, when undiluted hybridoma supernatant fractions were being screened, 40 ul of either 10% methanol in PBS (PBS-MEOH) or T-2 toxin (10 ug/ml) in PBS-MEOH were put in each well, followed by 40 ul of hybridoma supernatant. Supernatants from each colony tested were put in four wells, two with free T-2 and two without. When preparations other than undiluted hybridoma supernatants were assayed, this step instead consisted of adding 25 ul PBS-ovalbumin to each well, followed by 50 ul trichothecene in PBS-MEOH then 50 ul antibody preparation diluted in PBS. Washing followed a 1 hour incubation at 37° C. Next antimouse-peroxidase (80 ul when screening hybridoma supernatants and 100 ul at other times), diluted 1/500 in PBS +1% fraction V BSA (wt/vol) +0.1% Tween 20 was added, followed by a 30 minute incubation at 37° C. After washing, bound peroxidase was assayed by 10 incubating 100 ul ABTS-$H_2O_2$ substrate in each well for 5–30 minutes; the reaction was terminated with 100 ul stopping solution (Pestka, J. J., P. K. Gaur, and F. S. Chu., Appl. Environ. Microbiol. 40:1027–1031 (1980)). Absorbance at 405 nm was determined on an EIA reader EL307 (BioTech, Inc., Burlington, Vt).

Hybridoma Preparation. Dulbecco's modified eagle medium with 20% fetal bovine serum, and standard concentrations of penicillin, streptomycin, oxaloacetate, sodium pyruvate, insulin, B-mercaptoethanol, and NCTC (20% FBS) was routinely used as cell culture media. The mouse with the highest titer was injected intraperitoneally after five weeks rest with 300 ug T-2HS-BSA in 300 ul saline. The fusion protocol described by Oi and Herzenberg (Oi, V. T., and L. A. Herzenberg., Selected Methods in Cellular Immunology. W. H. Freeman, U.S.A. p. 351–372 (1980)) and the spleen cell preparation method of Kennett (Kennett, R. H., Monoclonal Antibodies, p. 365–367 (1980)) were followed. A total of 300 wells were seeded at $7\times10^5$ cells per well, with a B cell to myeloma ratio of 7:1. Supernatants were screened when the colonies were at least half-confluent. Positively tested colonies were expanded in 20% FBS, half of which had previously been conditioned by myeloma growth in log phase for 2 days, to which hypoxanthine and thymidine (HT) had been added (half strength conditioned media). Cloning was performed by limiting dilution in either half strength conditioned media or 20% FBS+HT which contained 30% myeloma conditioned and 20% macrophage conditioned (Sugasawara, R. J., B. E. Cahoon, and A. E. Karu., J. Immunol. Methods 79:263–275 (1985)) media. Ascites fluid was collected from pristane primed mice which were injected intraperitoneally with $10^7$ hybridoma cells in 0.5 ml 20% FBS twelve days earlier.

Monoclonal Antibody Characterization. The supernatant fraction from a colony that was cloned at 1 cell per well was precipitated three times in a 50% ammonium sulfate solution. The precipitated fraction was diluted sixteen-fold over the original supernatant volume and this was used in the CEIA described above. This fraction was also used with a Boehringer Mannheim subclass kit to determine the subclasses of the heavy and light chains of the antibody. RESULTS Immunization Protocols. Table 1 summarizes the results obtained when a 1/400 dilution of the mouse sera was tested with CEIA.

TABLE 1

Results of CEIA testing of diluted (1/400) mouse sera for T-2 polyclonal antibody activity. The results are based upon the relative intensity of light under ultraviolet ($^A$405) from substrate.

| Protocol[a] | Mouse | No free T-2[b] | Free T-2[c] | No specific coat[d] |
|---|---|---|---|---|
| A | 1 | 0.17 | 0.17 | 0.17 |
| | 2 | 0.15 | 0.19 | 0.14 |
| | 3 | 0.12 | 0.12 | 0.14 |
| B | 1 | 0.47 | 0.21 | 0.23 |
| | 2 | 0.61 | 0.70 | 0.60 |
| | 3 | 0.44 | 0.23 | 0.19 |

[a]Protocols: A = 100 ug T-2HS-BSA in 0.1 ml saline + 0.1 ml adjuvant interperitoneally at 1 month intervals. B = 0.5 to 1.0 mg T-2HS-BSA in 0.5 ml saline subcutaneously at two week intervals.
[b]10% methanol in PBS (PBS-MEOH) added with equal volumes of diluted serum.
[c]1 ug/ml T-2 in PBS-MEOH added with equal volumes of diluted serum.
[d]These wells were coated with a conjugate prepared similar to the T-2HS-PLL conjugate, except no T-2HS was used.

The mice injected by protocol A, which is a common immunization protocol, showed no activity against T-2 toxin, either in amount of antibody binding or in specific inhibition of antibody binding by free T-2. In contrast, strong specific binding was seen in mice 1 and 3, since free T-2 at lug/ml inhibited binding of antibody to background levels. Mouse 2 with this protocol showed nonspecific binding of antibody, since free T-2 could not inhibit binding, and also since wells coated with a conjugate that was not made with T-2 toxin had a similar amount of antibody binding (Table 1). Mouse 3 under protocol B was used in the fusion; at a dilution of 1/100, serum from this mouse showed stronger T-2 antibody activity than mouse 1.

. Hybridoma Preparation. The fusion efficiency (number of wells with clone/number of wells seeded) was greater than 95% (286/300). Of these, nine (3.1%)

showed strong specific binding to the T-2HS-PLL solid phase. Other colonies showed an equivalent amount of binding but this binding was not inhibited in the wells where free T-2 was present. The nine colonies showing specific binding were cloned at both one and five cells per well in half strength conditioned media. None of these clonings yielded a colony with stable T-2 antibody activity and eight of these either lost activity before they could be frozen or were no longer active when they were thawed. One colony did retain activity upon freezing and thawing and this was successfully cloned (one positive clone) at one cell per well in 20% FBS +HT with 30% myeloma conditioned and 20% macrophage conditioned media. This positive clone was quite stable, and all three surviving mice which were injected interperitoneally with this clone yielded ascites fluid which was active at a dilution of 1/5000 after ammonium sulfate precipitation. When cloned a second time to one cell per well, more than 90% of the colonies which grow showed specific binding.

Antibody Characterization. The antibody described above was a $IgG_1$ with a kappa light chain. Table 2 shows the results of tests of various trichothecenes for antibody reactivity.

TABLE 2

Sensitivity of T-2 reactive monoclonal antibody to various trichothecenes in CEIA[a]. The comparison was with controls based upon intensity of light under ultraviolet light.

| Trichothecene | Minimal Inhibition[b] | 50% Inhibition[c] |
|---|---|---|
| T-2 | 0.01 | 0.023 |
| T-2HS | 0.01 | 0.072 |
| Acetyl T-2 | 0.01 | 0.094 |
| 3'OH T-2 | 0.005 | 0.018 |
| 3'OH HT-2 | 0.05 | 0.100 |
| HT-2 | 0.5 | 1.0 |
| Neosolaniol | 1.0 | 1.6 |
| T-2 triol | 5.0 | 14.9 |
| T-2 tetraol | 100. | 447. |
| Verrucarol | 500. | >500. |
| Deoxynivalanol | >1000. | >1000. |
| Roridin A | >5000. | >5000. |

[a]All values are in ug/ml of trichothecene in 10% methanol/PBS.
[b]ug/ml trichothecene in methanol. PBS required for first significant inhibition of binding of antibody to the T-2HS-ovalbumin solid phase.
[c]ug/ml trichothecene required to inhibit binding of antibody by 50% to the T-2HS-ovalbumin solid phase. See text or Appendix B for assay protocol. Includes only trichothecenes with 50% inhibition at less than 10 ug/ml.

This antibody has less reactivity to HT-2 toxin relative to T-2 (2%) than other T-2 antibodies described (Chu, F. S., S. Grossman, R.-D. Wei, and C. J. Irocha. Appl. Environ, Microbiol. 37:104–108 (1979); and Gendloff, E. H., J. J. Pestka, S. P. Swanson, and L. P. Hart. Appl. Environ. Microbiol. 47:1161–1163 (1984)). A strong cross reaction was found with the 3'OH metabolites of T-2 and HT-2 as well as with acetyl T-2 (Table 2). The aforementioned metabolites have not been tested using other antibodies, but other trichothecenes tested (other than HT-2) have similar percentage cross reactivities relative to T-2 (Chu, F. S., S. Grossman, R.-D. Wei, and C. J. Irocha. Appl. Environ. Microbiol. 37:104–108 (1979); and Gendloff, E. H., J. J. Pestka, S. P. Swanson, and L. P. Hart. Appl. Environ. Microbiol. 47:1161–1163 (1984)). Sensitivity to T-2, at 0.01 ug/ml., was 0.5 ng/assay, which was less sensitive than systems using rabbit antisera (Chu, F. S., S. Grossman, R.-D. Wei, and C. J. Irocha. Appl. Environ. Microbiol. 37:104–108 (1979); and Gendloff, E. H., J. J. Pestka, S. P. Swanson, and L. P. Hart. Appl. Environ. Microbiol. 47:1161–1163 (1984); Fan, T. S. L., G. S. Zhang, and F. S. Chu., J. Food Protection 47:964–967 (1984); Fontelo, P. A., J. Beheler, D. L. Bunner, and F. S. Chu., Appl. Environ. Microbiol. 45:640–642 (1983); and Pestka, J. J., S. L. Lee, H. P. Lau, and F. S. Chu., J. Am. Oil Chem. Soc. 58:940A–944A (1981)). However, the sensitivity was sufficient for assay purposes and the monoclonal antibodies were easier to produce.

Procedure for Freezing and Thawing Hybridomas

25 Thawing of the Cells: The cryovial was removed from the liquid nitrogen. The culture was thawed as quickly as possible. The bottom of the cryovial was immersed in a 37° C. water bath and it was agitated until the contents were just barely thawed. The exterior of the vial was wiped down with 70% EtOH and the contents were placed in a 15 ml conical tube which had been cooled on ice. Cold 20% FBS-DMEM (10 ml) was added dropwise over a period of about two minutes. The cells were centrifuged at 450×g for eight minutes at 4° C. The centrifugation can be performed at room temperature if a refrigerated centrifuge is not available. The supernatant was removed and the pellet was resuspended in 5 ml of 20% FBS-DMEM. The suspension can be placed into a 25 $cm^2$ tissue culture flask, or preferably, it should be added to a 24 well plate divided into four aliquots (1.25 ml). The plate was incubated at 37° C. in an atmosphere of 8% $CO_2$. The culture was fed as necessary and transferred from the plate to a small T-flask. The culture was maintained at $1\times10^5$ cell/ml.

Freezing of the Cells: All materials were cooled on ice during the procedure. The appropriate volume of culture containing $1\times10^6$ cells was placed in a 15-ml conical tube and centrifuged at 450×g for eight minutes at room temperature. The supernatant was removed and the pellet was resuspended in 0.5 ml of freezing medium. The cryovial was placed in a rack or can which was placed in a styrofoam box and cooled in a −80° C. freezer. Twenty-four hours later the culture was transferred to liquid nitrogen.

Media:

1. Dulbecco's minimal eagle's medium (DMEM): DMEM was reconstituted according to the instructions supplied by Gibco, Grand Island, N.Y. Supplements were added to make complete DMEM (10 mM sodium pyruvate, 1% NCTC, 5 mM oxaloacetate, and insulin (75.5 mg/L)).

2. 20% FBS-DMEM: Prepared by adding 20 ml of fetal bovine serum (FBS) and 1 ml of penicillin/streptomycin solution (100.000 U/ml) to 80 ml of complete DMEM. Filter sterilized and store at 4° C.

3. Freezing Medium: Mixed 10 ml of dimethyl sulfoxide (DMSO) and 90 ml of FBS. Filter sterilized and stored at −20° C.

DISCUSSION

The immunization protocol used, in which large antigen doses were given subcutaneously without adjuvant, was clearly superior to the more traditional interperitoneal immunization protocol tested (Table 1). Two of the three mice immunized with the former protocol showed titers at the dilution tested, whereas none of the mice immunized with the latter protocol did. The nonspecific binding shown by serum of mouse B2 (Table 1) illustrates that antibody binding does not necessarily mean a specific reaction has taken place. As stated previously, when the hybridoma supernatant fractions were being tested, antibody binding would sometimes occur that could not be inhibited with free T-2 toxin. Routine employment of the competitive free T-2 procedure crucial was essential in preventing false positives.

There was high fusion efficiency and a reasonable number of positive colonies. The preferred subcutaneous immunization protocol overcame possible immunotoxicity. The major problem was in retaining a stable colony through cloning. Although the half strength conditioned media allowed very high cloning efficiencies when myeloma as well as these hybridoma lines were cloned, no positive colony could be had until we included macrophage conditioned media, produced by the method of Sugasawara et al (Sugasawara, R. J., B. E. Cohoon, and A. E. Karu, J. Immunol. Methods 79: 263–275 (1985)) as included. Presumably, the hybridoma of interest needed growth factors present in the macrophage conditioned media but not the myeloma conditioned media.

As stated before, the antibody shows cross-reactivities similar to T-2 antibodies previously characterized, except for its relatively weak cross-reaction to HT-2 (Table 2). These differing specificities are useful in assaying for T-2 in biological systems. If samples were assayed with two antibodies of different specificities, the relative amounts of each trichothecene could be determined. A series of monoclonals can be obtained, each with different specificities for many trichothecenes.

The strong cross-reactivities to the 3'OH metabolites of T-2 and HT-2 means that this antibody can be used in assays of T-2 toxicosis, since these metabolites are diagnostic and present in significant amounts when T-2 toxicosis occurs.

Assays

The following describes the actual use of the T-2 monoclonal antibody in an assay for T-2 toxin in a naturally contaminated samples of wheat and corn:

1. Preparation of T-2 antibody coated plates:
   a. T-2 monoclonal antibody was diluted 1:50 in carbonate coating buffer (pH 9.6) and 50 ul aliquots dried onto each well of 96-well micro-titer immunoassay plates.
   b. After drying, the plates were washed three times with 0.05% tween-20 in 0.1 M Phosphate buffered Saline (PBS-Tween: pH 7.5).
   c. Each well was then blocked to remove sites on the plate not blocked by the antibody by adding 200 ul of 1% bovine serum albumin (BSA), incubating for one hour at 37° C., and then washing two more times with PBS-tween and one time with distilled water.

2. Sample Preparation:
   a. Four samples (three corn and one wheat) were ground dry in a waring blender, weighed and extracted with five volumes of Methonal:water (40:60).
   b. After filtering through filter paper, 50 ul of the liquid extractant was mixed with an equal volume of T-2 Horse Radish Peroxidase conjugate (T-2HRP), and pipetted into the antibody coated wells (100 ul/well). T-2 HRP was diluted 1:50 in 1% BSA before mixing with sample.
   c. After 10 minutes incubation at room temperature the wells were aspirated and washed 10 times with distilled water.
   d. ABTS substrate was added, 100 ul per well, and incubated 20 minutes, after which 100 ul of stopping reagent was added, and absorbance of each well determined with an ELISA plate reader. The stopping reagent was as follows:

| | |
|---|---|
| Distilled water | 80 ml |
| Hydroflouric Acid | 0.315 ml |
| 1N Sodium hydroxide soln. | 0.54 ml |
| EDTA (tetra sodium salt) | 36 milligrams |

The reagent was adjusted pH to 3.0 with NaOH or HCl.

Sufficient distilled water was added to bring the volume to 90 ml.

e. Controls consisted of adding known concentrations of T-2 standards to extracts of clean corn and using these to mix with the T-2 HRP in the wells. The four samples consisted of two corn samples infected with *Fusarium graminearum* (which does not produce T-2 toxin), and one corn and one wheat sample infected with *F. sporotrichoides* (a producer of T-2 toxin).

3. Results:
   a. Based on a comparison of absorbance readings the concentration of T-2 toxin in the samples was:

| *F. graminearum* infected grain (1) <10 ng/g | |
|---|---|
| *F. sporotrichoides* infected grain corn - 100 ng/g | |
| wheat - <10 ng/g | |
| Standard (ng/ml) or sample | Absorbance (ave. of 3) |
| 0 | 1.093 |
| 1 | 0.967 |
| 10 | 0.471 |
| 100 | 0.147 |
| 1000 | 0.057 |
| *F. graminearum* (1) | 0.507 |
| *F. graminearum* (2) | 0.773 |
| *F. sporotrichoides* - corn | 0.137 |
| *F. sporotrichoides* - wheat | 1.074 |

Obvious variations will occur to those skilled in the art since the art of preparing hybridomas, monoclonal antibodies and the use thereof in test kits is well developed in the patent arts and literature. It is intended that the present invention be limited only by the hereinafter appended claims.

We claim:

1. An immunoassay test kit for detecting trichothecene mycotoxin T-2 in a sample comprising monoclonal antibody with all the identifying characteristics of the monoclonal antibody produced by hybridoma IVI-10092 or said monoclonal antibody labeled with a detectable moiety.

2. An immunoassay method for the detection of trichothecene mycotoxin T-2 in a sample comprising contacting said sample with monoclonal antibodies having all the identifying characteristics of the monoclonal antibodies secreted by hydridoma IVI-10092 under conditions leading to the formation of immunological complexes and detecting the formation of said complexes.

3. The hydridoma identified as IVI-10092.

4. The monoclonal antibody produced by the hybridoma identified as IVI-10092.

5. The test kit of claim 1 wherein said detectable moiety is an enzyme, and said enzyme is conjugated to said monoclonal antibody or to trichothecene mycotoxin T-2.

6. The test kit of claim 1 wherein said monoclonal antibody is bound to a solid phase, said detectable moiety is an enzyme, and said enzyme is conjugated to trichothecene mycotoxin T-2.

7. The test kit of claim 1, wherein said detectable moiety is an enzyme, said enzyme is conjugated to said monoclonal antibody, and further comprising a conjugate of trichothecene mycotoxin T-2 and a polypeptide, said conjugate is bound to a solid phase.

8. The test kit of claim 5 wherein said enzyme is peroxidase.

9. The method of claim 2 wherein said monoclonal antibodies are bound to a solid phase, and said detecting comprises adding a known amount of a trichothecene mycotoxin T-2 conjugated to an enzyme to said sample to compete with any trichothecene mycotoxin T-2 in said sample to form complexes with said antibodies.

10. The method of claim 2 wherein said monoclonal antibodies are conjugated to an enzyme, and said detecting comprises adding said antibody to said sample, wherein said sample is in contact with a solid phase bound conjugate of trichothecene mycotoxin T-2 and a polypeptide, said conjugate competes with any trichothecene mycotocin T-2 in said sample to form complexes with said antibodies.

* * * * *